United States Patent
Lee (10) Patent No.: US 7,693,316 B2
(45) Date of Patent: Apr. 6, 2010

(54) APPARATUS AND METHOD FOR DISPLAYING HOLOGRAM OF A MOBILE COMMUNICATION TERMINAL

(75) Inventor: Tae Hyo Lee, Seoul (KR)

(73) Assignee: Pantech & Curitel Communications, Inc., Seoul (KR)

( * ) Notice: Subject to any disclaimer, the term of this patent is extended or adjusted under 35 U.S.C. 154(b) by 1161 days.

(21) Appl. No.: 10/943,482

(22) Filed: Sep. 17, 2004

(65) Prior Publication Data

US 2005/0110866 A1    May 26, 2005

(51) Int. Cl.
*G06K 9/00*    (2006.01)

(52) U.S. Cl. ............... 382/128; 348/14.01; 348/14.02; 348/14.03; 348/14.04; 348/14.05; 348/14.07; 348/14.08; 348/14.09; 348/14.1; 348/14.12; 348/14.16; 359/1; 359/9; 359/10; 359/11; 359/15; 359/35

(58) Field of Classification Search ............... 348/14.01, 348/14.02, 14.07, 14.12, 40, 14.03, 14.04, 348/14.05, 14.06, 14.08, 14.09, 14.1, 14.11, 348/14.13, 14.14, 14.15, 14.16; 359/1, 9, 359/10, 11, 15, 35; 382/128
See application file for complete search history.

(56) References Cited

U.S. PATENT DOCUMENTS

| | | | | |
|---|---|---|---|---|
| 5,097,323 A * | 3/1992 | Sato et al. | ................... | 348/761 |
| 5,315,377 A * | 5/1994 | Isono et al. | ................... | 348/51 |
| 5,441,047 A * | 8/1995 | David et al. | ................. | 600/301 |
| 5,631,750 A * | 5/1997 | Minoura et al. | ............. | 349/110 |
| 5,868,480 A * | 2/1999 | Zeinali | ........................ | 353/31 |
| 6,007,459 A * | 12/1999 | Burgess | ..................... | 600/301 |
| 2003/0023175 A1* | 1/2003 | Arzbaecher et al. | ......... | 600/509 |
| 2004/0058715 A1* | 3/2004 | Taniguchi et al. | ........... | 455/566 |

* cited by examiner

*Primary Examiner*—Vikkram Bali
*Assistant Examiner*—Daniel Zeilberger
(74) *Attorney, Agent, or Firm*—H.C. Park & Associates, PLC

(57) ABSTRACT

Disclosed are an apparatus and a method for displaying hologram of a mobile communication terminal. The present invention can create hologram from two-dimensional image by providing a hologram processing function for a mobile communication terminal and provide the hologram to a user. Further, the mobile communication terminal with the hologram processing function can perform medical diagnosis on a user, and thus can save a life by performing accurate medical diagnosis in emergency through hologram communication with an emergency center.

10 Claims, 5 Drawing Sheets

APPARATUS AND METHOD FOR DISPLAYING HOLOGRAM OF A MOBILE COMMUNICATION TERMINAL

CROSS REFERENCE TO RELATED APPLICATION

This application claims priority from and the benefit of Korean Patent Application No. 10-2003-0084051, filed on Nov. 25, 2003, which is hereby incorporated by reference for all purposes as if fully set forth herein.

BACKGROUND OF THE INVENTION

1. Field of the Invention

The present invention relates to a mobile communication terminal, and more particularly to an apparatus and a method for displaying hologram of a mobile communication terminal having a hologram display function, thereby enabling hologram communication.

2. Description of the Related Art

In the prior art, a hologram technology for a mobile communication terminal relates to manually replacing a LCD panel for making two-dimensional image be seen as stereoscopic picture. Also, a television or a display apparatus with large screen is actually required to provide the stereoscopic picture from two-dimensional image received for a user. Thus, there are problems such as space, accuracy etc.

SUMMARY OF THE INVENTION

Accordingly, the present invention has been made to solve the above-mentioned problems occurring in the prior art. The object of the present invention is to create hologram from two-dimensional image by providing a hologram processing function for a mobile communication terminal and to provide the hologram to a user.

The other object of the present invention is to perform remote medical diagnosis on a user with a mobile communication terminal having a hologram processing function and to enable hologram communication with an emergency center.

In order to accomplish the objects, there is provided a hologram displaying apparatus of a mobile communication terminal comprising: a RF processing section for wirelessly transmitting/receiving data; a camera section for demodulating digital image data imputed with an image processing; a backup section for backing up and outputting demodulated image data; a control section for demodulating image data received through the RF processing section at a hologram mode so as to output corresponding digital image data to the camera section and making the backup section output the backup data; a panel interface section for receiving the image data outputted from the backup section, image-processing the received data and then outputting the image-processed data; and a hologram processing section for projecting hologram using the image data outputted from the panel interface section.

Preferably, the hologram processing section comprises a light source generating section for generating light; a optical switching section for switching the light according to the image data and outputting two-dimensional image signal; a hologram displaying section for creating and displaying hologram from the two-dimensional image signal by using difference of angle of vision between two eyes; and a light source lens for enlarging and projecting the hologram to space.

Further, preferably, the optical switching section comprises a digital micromirror device for receiving red light, a digital micromirror device for receiving blue light, and a digital micromirror device for receiving green light through the optical switching.

Preferably, the hologram displaying section comprises image pixels separated from each other with a predetermined gap and transmitting the two-dimensional image signal; and a mask pitch comprising transparent slits and lattice pattern and projecting the two-dimensional image signal to the light source lens through the transparent slits.

Alternatively, the hologram processing section comprises a light-emitting lamp; a red mirror, a green mirror and a blue mirror separating the light into primary color light of red, green and blue, respectively, according to the image data; a mono liquid crystal panel for reflecting light of other colors than the primary colors and projecting only the primary color light; a LCD panel for resynthesizing the projected light of the primary colors so as to create two-dimensional image; a combiner tube for creating hologram from the two-dimensional image by color combination; and a lens for enlarging and projecting the created hologram.

More preferably, the present mobile communication terminal having a hologram display function further comprises a medical diagnosis section for performing medical diagnosis on a user of the terminal and outputting corresponding diagnosis data and a displaying section for receiving the diagnosis data and displaying it to the user according to control of the control section.

Preferably, the control section compares the diagnosis data with a previously stored medical reference value, and transmits the diagnosis data to a preset emergency center through the RF processing section when it determines the user's condition as abnormal. Also, the control section converts a mode of the terminal into a hologram mode according to a choice of the user, and transmits image data regarding the user photographed through the camera section to the emergency center through the RF processing section.

Also, preferably, the control section demodulates analog image data received from the emergency center through the RF processing section and outputs corresponding digital image data to the camera section and makes the backup section output the backup data.

According to another aspect of the invention, there is provided a method for displaying hologram of a mobile communication terminal comprising processes of performing medical diagnosis on a user through a medical diagnosis section contacting with the user and outputting corresponding diagnosis data; comparing the diagnosis data with a previously stored medical reference value and setting up call with a preset emergency center to transmit the diagnosis data to the center, in the case of an abnormal state as a result of the comparison; photographing the user through a camera section according to a choice of the user and transmitting corresponding image data to the preset emergency center to digital image data; and demodulating analog image data received from the emergency center, creating hologram using the demodulated digital image data and displaying the hologram to the user.

Preferably, the process of displaying the hologram comprises steps of backing up and image-processing the digital image data; switching light projected from light source according to the processed image data and projecting the light to transparent slits of a mask pitch through image pixels to display the hologram; and enlarging the hologram through a light source lens and projecting the enlarged hologram to space.

Preferably, digital micromirroe devices are used to receive red light, blue light and green light when switching the light projected from the light source.

Alternatively, the process of displaying hologram comprises steps of backing up and image-processing the digital image data; separating light emitted from a lamp into primary color light of red, green, and blue by a red mirror, a green mirror and a blue mirror according to the processed image data; reflecting light of other colors than the primary colors of the separated light and projecting only the primary color light by a mono liquid crystal panel; resynthesizing the projected respective primary color light to create two-dimensional image by a LCD panel; creating hologram from the two-dimensional image through color combination by a combiner tube; and enlarging and projecting the created hologram by a lens.

BRIEF DESCRIPTION OF THE DRAWINGS

The above and other objects, features and advantages of the present invention will be more apparent from the following detailed description taken in connection with the accompanying drawings, in which.

DETAILED DESCRIPTION OF THE PREFERRED EMBODIMENTS

Hereinafter, preferred embodiment of the present invention will be described with reference to the accompanying drawings. In the following description of the present invention, a detailed description of known functions and configurations incorporated herein will be omitted when it may make the subject matter of the present invention rather unclear.

Figure 1:
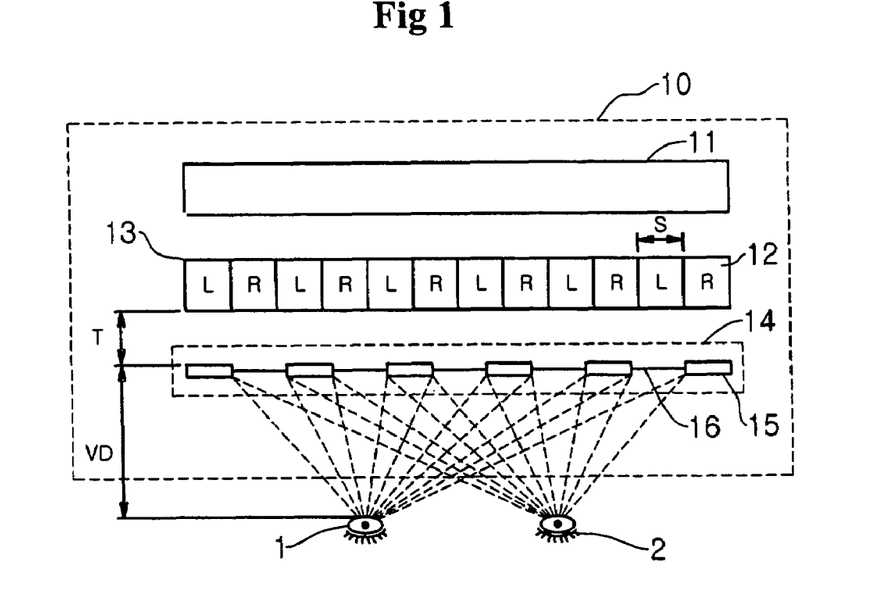
FIG. 1 is a view showing a structure of a hologram-generating apparatus applied to the present invention.

FIG. 1 is a view showing a structure of a hologram-generating apparatus applied to the invention.

Referring to FIG. 1, the hologram-generating apparatus 10 comprises a backlight light source 11, an image panel 13 and a mask pitch 14. The image panel 13 comprises two-dimensional image pixels 12 separated from each other with a predetermined gap S. The mask pitch 14 comprises masks 15 and transparent slits 16, wherein each transparent slit 16 is located at the middle boundary of every two image pixels 12, and the mask 15 is located at the front of the image panel 13 with a predetermined distance T.

An overall size P of the mask pitch 14 is prepared using the following formula in consideration of the gap S of image pixels 12, the distance T between the image panel 13 and the mask 15, and a distance VD between a transparent slit 16 and an observer.

$$P = 2S(VD-T)VD \quad \text{Formula 1}$$

Since a distance between a left eye 1 and a right eye 2 of a person is about 6.5 cm, horizontal angles of the line of vision are different when looking at an object. Thus, when the image pixels 12 respectively recorded at different horizontal angles are separated with a predetermined gap, and each separated image pixel 12 is integrated to maintain an inherent horizontal angle and then is seen through the mask pitch 14, images of two eyes 1 and 2 are seen at different angle, respectively. Image with such binocular parallax is recognized as a stereoscopic image by a brain.

Figure 2:
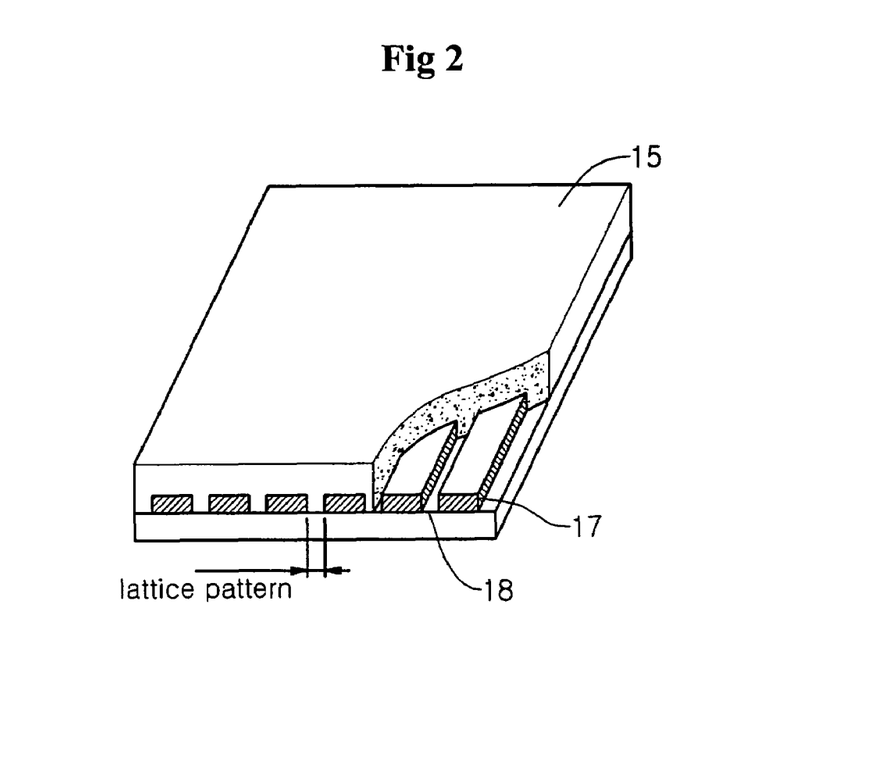
FIG. 2 is a cross section of a parallax barrier mask used in the hologram-generating apparatus.

FIG. 2 is a cross section of a parallax barrier mask 15 used in the hologram-generating apparatus 10.

Referring to FIG. 2, the mask 15 comprises a transparent adhesive 17, which forms a transparent area by backlight light source 11, and a film base 18 using lattice pattern forming an opaque area.

Material for the film base 18 is usually polyethylene terephthalate (PFT), and total thickness of the lattice pattern is about 170~400 micron. Material for transparent adhesive 17, which is used to prevent optical scattering of the film base, is polycarbonate (PC, about 200~500 micron). Also, resinous film, glass, and ceramic etc. can be used as a transparent material.

Figure 3:
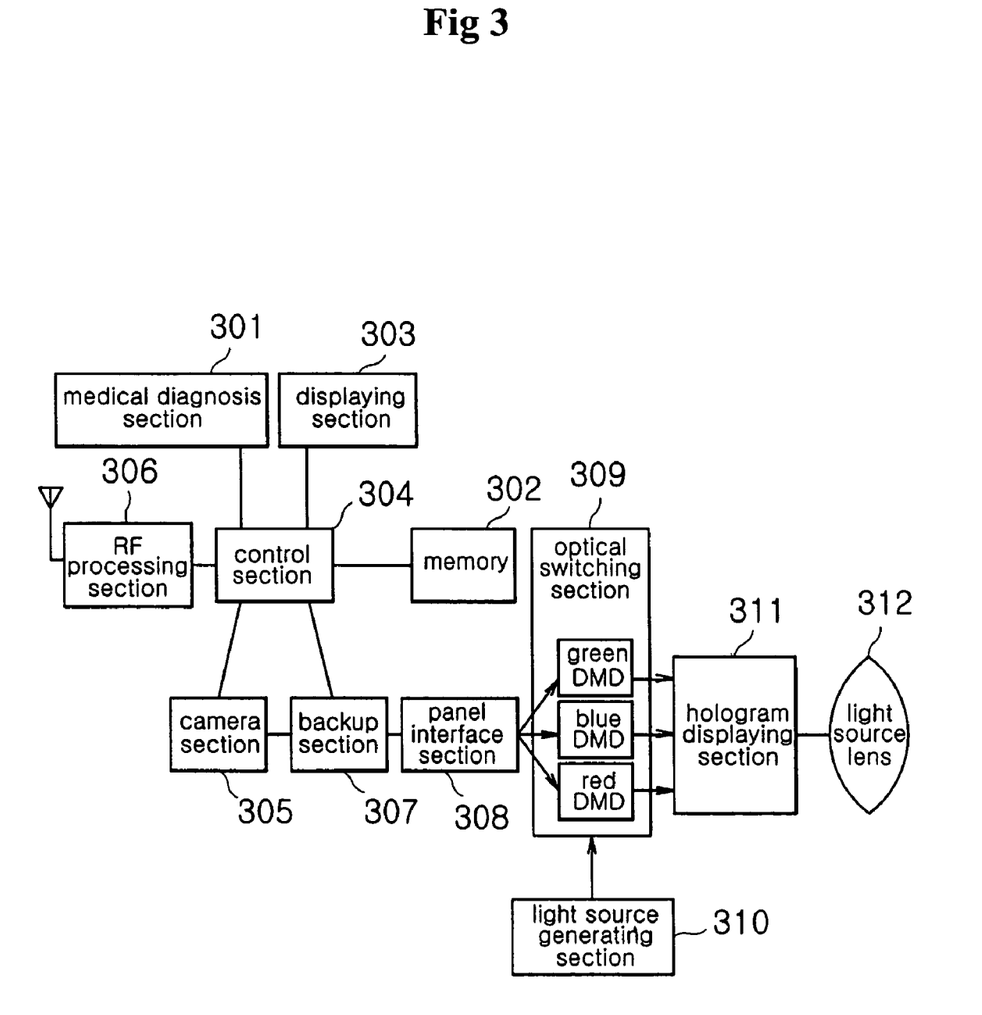
FIG. 3 is a block diagram showing a structure of a hologram-displaying apparatus of a mobile communication terminal according to one embodiment of the present invention.

FIG. 3 is a block diagram showing a structure of a hologram-displaying apparatus of a mobile communication terminal according to one embodiment of the invention.

Referring to FIG. 3, the hologram-displaying apparatus of the embodiment comprises a medical diagnosis section 301, a memory 302, a displaying section 303, a control section 304, a camera section 305, a RF processing section 306, a backup section 307, a panel interface section 308, a optical switching section 309 performing a hologram processing function 309, a light source generating section 310, a hologram displaying section 311 and a light source lens 312.

The medical diagnosis section 301 diagnoses body temperature or blood pressure of a user through a contact with skin, and transfers the diagnosis data to the control section 304 via an input-output interface section (not shown).

The control section 304 compares the diagnosis data transferred from the medical diagnosis section 301 with a medical reference value previously stored in the memory 302. When the data is above the reference value, i.e., body temperature or blood pressure of the user is high, the control section displays the diagnosis data on the displaying section 303, and automatically sets up call with a preset emergency center (not shown) through the RF processing section 306. At this time, the diagnosis data is transmitted to the emergency center.

Further, depending on a choice of the user who wants a medical checkup, the control section converts a mobile communication terminal into a hologram mode, and transmits image data of the user photographed by means of the camera section 305 to the emergency center through the RF processing section 306 after processing the image data.

Meanwhile, the control section 304 demodulates image packet data which is an analog signal received from the emergency center through the RF processing section 306 to a digital signal, and transmits the demodulated digital signal to the camera section 305 for real-time image processing.

The camera section 305 demodulates the digital signal transmitted from the control section 304 to image data through an image processing, and transmits the demodulated image data to the backup section 307 embodied as a back end-chip.

The backup section 307 transmits the demodulated image data to the panel interface section 308 after a data regulation in accordance with a request of the control section 304. The panel interface section 308 performs an image processing of brightness, coloring etc. regarding screen of the image data and then transmits the processed image data to the optical switching section 309.

The optical switching section 309 comprises a blue digital micromirror device (BLUE DMD) for receiving blue light, a green digital micromirror device (GREEN DMD) for receiving green light, and a red digital micromirror device (RED DMD) for receiving red light, which are small microchips to which hundreds of thousands of micro aluminum mirrors (not shown) are attached. These digital micromirror devices are projection type standard devices, which control light projected from the light source generating section 310, show brightness of each image pixel and output corresponding image signal. The digital micromirror device is optical switch in which micro driving mirrors are integrated.

In particular, the micro aluminum mirrors generate motion picture image by switching existing location, and the digital micromirror device scans the motion picture image from light collected on the surfaces of the micro aluminum mirrors through a lens (not shown).

The hologram displaying section 311 comprises an image panel 13 and a mask pitch 14 having masks 15 and transparent slits 16, as shown in FIG. 1, so that it projects an image signal inputted from the optical switching section 309 through the image pixels 12 of the image panel 13, i.e. two-dimensional image signal whose source is light of the light source generating section 310 through the transparent slits 16.

The light source lens 312 enlarges three-dimensional hologram signal projected from the hologram displaying section 311 and projects it to space.

Figure 4:
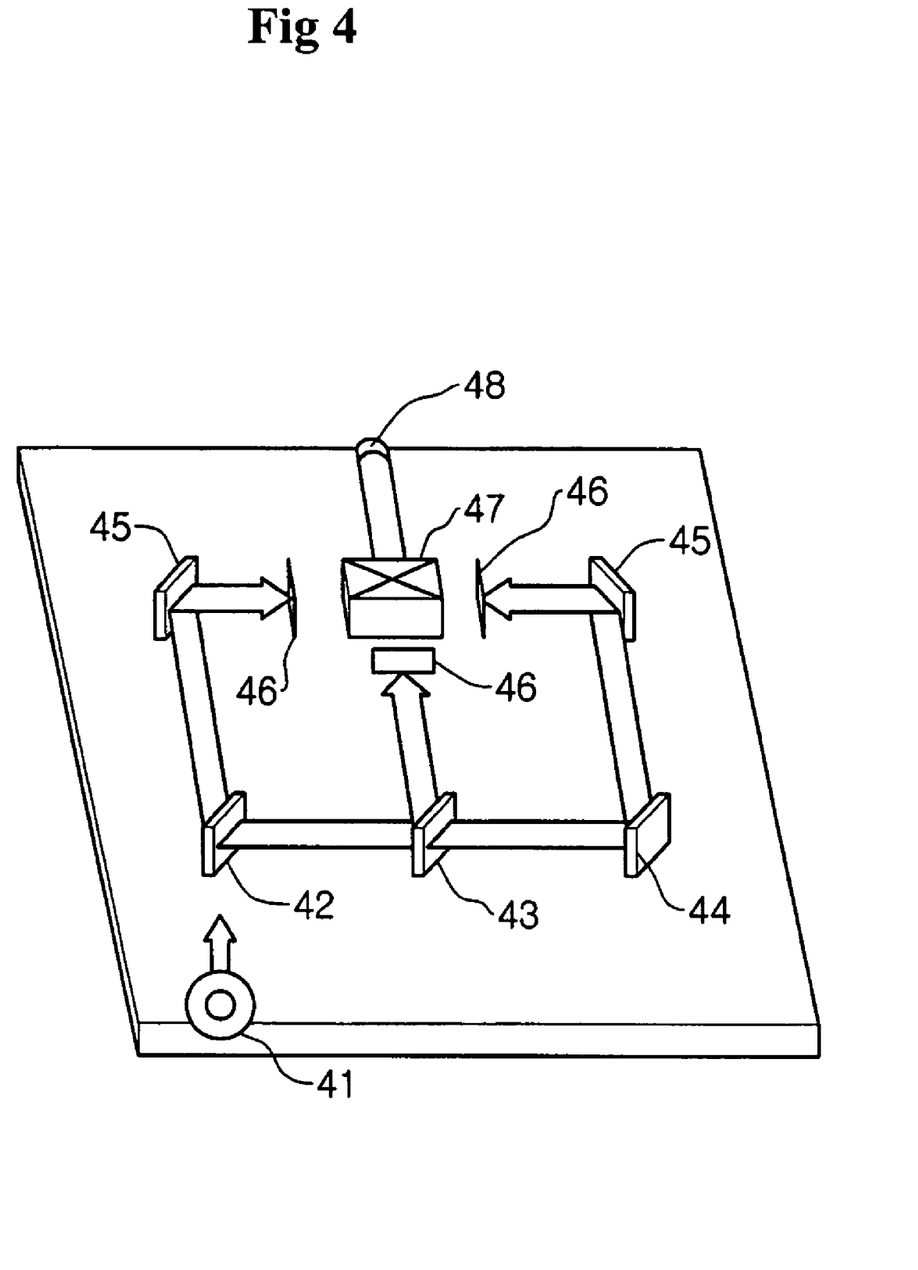
FIG. 4 is a block diagram showing a structure of a hologram processing section using a LCD panel in FIG. 3.

FIG. 4 is a view showing a hologram processing section adopting a lens-enlarging method using a LCD panel, which is different from a lens enlargement method using the digital micromirror device in terms of principle of light reflection.

Referring to FIG. 4, in the method using a LCD panel, according to an image signal having passed the panel interface section 308, light emitted from a lamp 41 is separated into red light, green light and blue light by a red mirror 42, a green mirror 43 and a blue mirror 44, and the separated light of primary colors are passed through a mono liquid crystal panel 45 which reflects other colors than the primary colors in a natural color. And then, the light of primary colors are resynthesized into two-dimensional image through each LCD panel 46.

The resynthesized two-dimensional image is inputted into a combiner tube 47, which is a two color combinator for synthesizing image colors having passed each LCD panel 46. The combiner tube 47 generates hologram using the inputted two-dimensional image, and projects the hologram through a lens 48.

Figure 5:
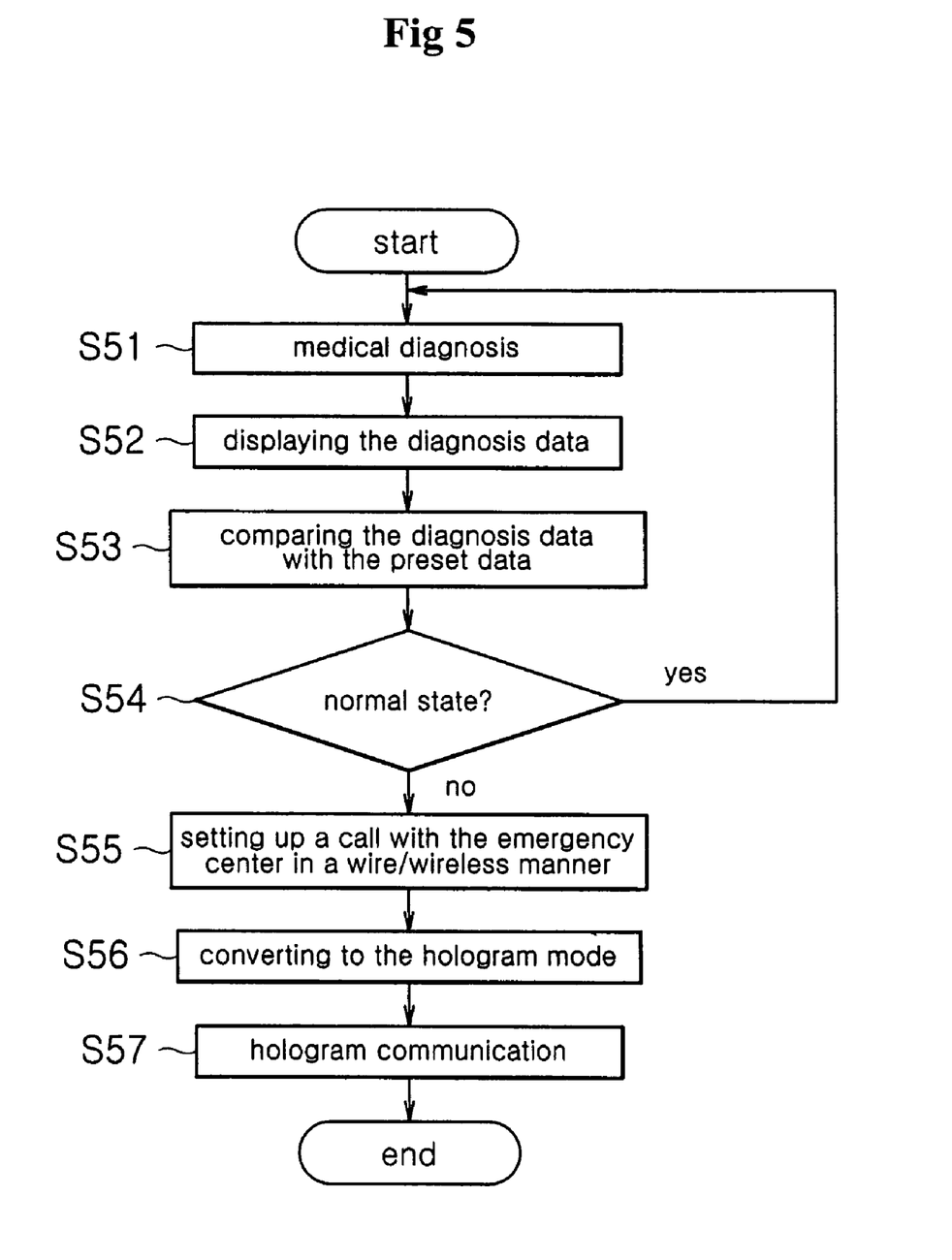
FIG. 5 is a flowchart showing a medical diagnosis procedure using a mobile communication terminal having a hologram display function according to one embodiment of the present invention.

FIG. 5 is a flowchart showing a medical diagnosis procedure using a mobile communication terminal having a hologram display function according to one embodiment of the invention.

Referring to FIG. 5, the control section 304 receives diagnosis data regarding body temperature or blood pressure of a user from the medical diagnosis section 301 which contacts with the skin of the user and performs medical diagnosis (S51).

And, the control section displays the inputted diagnosis data through the displaying section 303 (S52), and then compares the diagnosis data with reference data preset in the memory 302 (S53). The reference data is a medical reference value for body temperature or blood pressure of a normal person.

As a result of the comparison, when the condition is normal, the medical diagnosis is performed again (S54, S51), and when the condition is abnormal, setting up call with a preset emergency center is automatically performed in a wire or wireless manner (S54, S55).

Further, depending on the necessity of accurate medical checkup, according to key data entered by the user, the mobile communication terminal is switched to a hologram mode (S56), and hologram communication with the emergency center is performed (S57).

Figure 6:
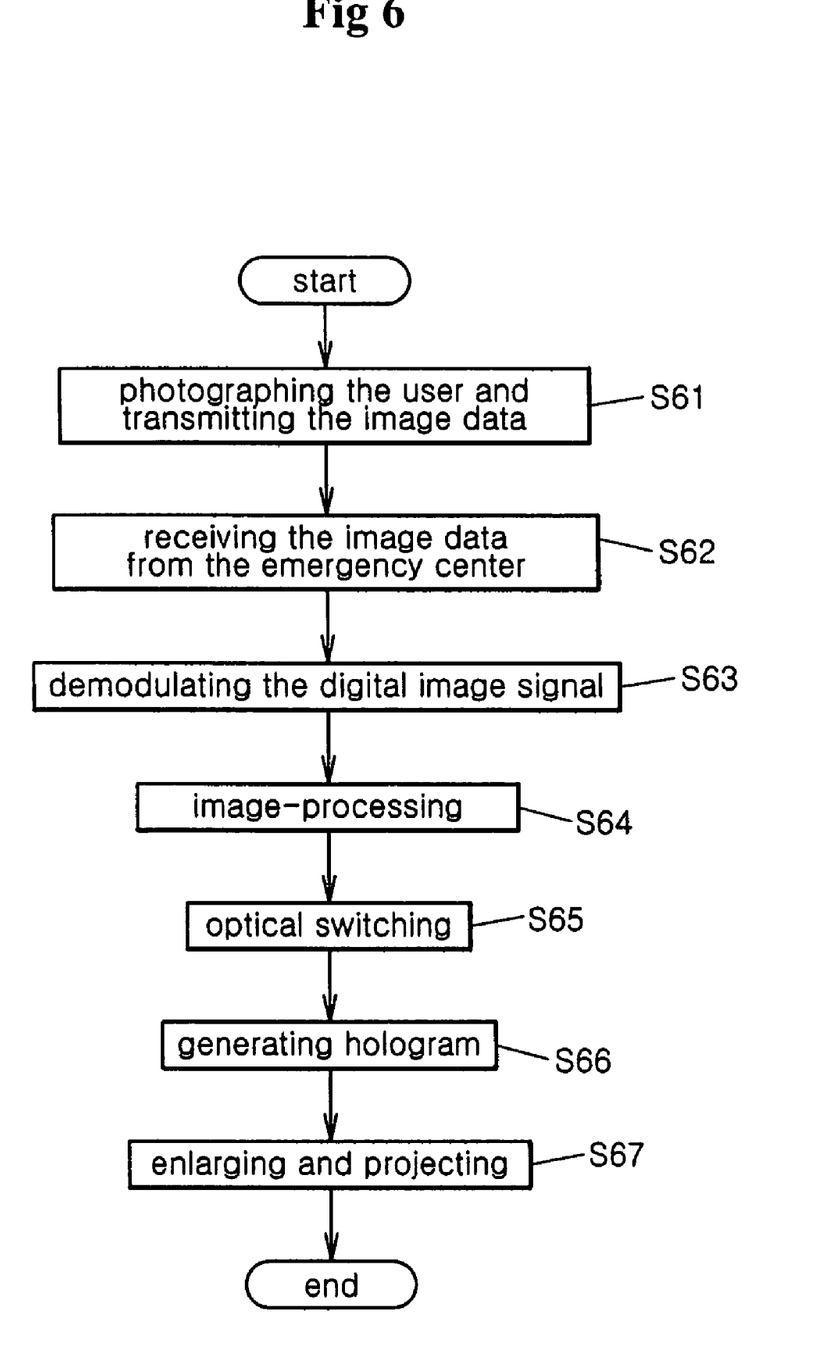
FIG. 6 is a flowchart showing a hologram communication procedure in FIG. 5.

FIG. 6 is a flowchart showing hologram communication procedure of a mobile communication terminal according to one embodiment of the invention.

Referring to FIG. 6, the control section 304 photographs a user through the camera section 305 in accordance with a choice of the user, and transmits the image data to the emergency center through the RF processing section 306 (S61).

And, the control section receives analog image data from the emergency center through the RF processing section 306 (S62), demodulates the analog image data to digital image data through the camera section 305 and then outputs the demodulated data to the backup section 307 (S63).

Then, the backup section 307 performs image processing of the digital image data and outputs the image data to the panel interface section 308 according to control of the control section 304. The panel interface section 308 performs image processing of the image data and then outputs the processed data to the optical switching section 309 (S64).

The optical switching section 309 switches light projected from the light source generating section 310 in accordance with the image data inputted from the panel interface section 308 so as to create two-dimensional image signal and then outputs the created signal to the hologram displaying section 311 (S65).

The hologram displaying section 311 creates hologram from the two-dimensional image signal using difference of angle of vision between two eyes (S66), and enlarges the hologram through the light source lens 312 and projects the enlarged hologram to space (S67).

As described above, the present invention can create hologram from two-dimensional image and provide it to a user by providing a hologram processing function for a mobile communication terminal.

Further, the mobile communication terminal having the hologram processing function can perform medical diagnosis on a user, and thus can save a life by performing accurate medical diagnosis in emergency through hologram communication with an emergency center.

While the invention has been shown and described with reference to contain preferred embodiment thereof, it will be understood by those skilled in the art that various changes or modifications in form and details may be made therein without departing from the spirit and scope of the invention as defined by the appended claims.

What is claimed is:

1. A hologram displaying apparatus of a mobile communication terminal, comprising:

a RF processing section to wirelessly transmit and receive data;

a camera section in the mobile communication terminal to capture a photographic image and to demodulate digital image data inputted with an image processing;

a backup section in the mobile communication terminal to back up and output the demodulated image data;

a control section to demodulate analog image data received through the RF processing section in a hologram mode to output the corresponding digital image data to the camera section, and to control the backup section to output backup image data;

a panel interface section to receive the image data outputted from the backup section, to image-process the received image data, and to output the image-processed image data;

a medical diagnosis section to perform medical diagnosis on a user of the terminal and to output corresponding diagnosis data; and a hologram processing section in the mobile communication terminal to project a hologram created from a two-dimensional image signal by using the image data outputted from the panel interface section, wherein the hologram processing section comprises:

an image panel having a plurality of image pixels separated from each other with a predetermined gap; and a mask pitch having masks and a plurality of transparent slits, wherein each transparent slit is located at a middle boundary of every two image pixels, and the mask pitch is located at the front of the image panel with a predetermined distance, wherein the control section compares the diagnosis data with a previously stored medical reference value, and transmits the diagnosis data to a preset emergency center through the RF processing section only if the user's condition is abnormal, and wherein the control section demodulates analog image data received from the preset emergency center by the RF processing section to digital image data, the panel interface section performs image processing of the digital image data, and the hologram processing section creates a hologram from a two-dimensional image signal created from the image processed digital image data and projects the hologram.

2. The apparatus according to claim 1, wherein the hologram processing section further comprises:

a light source generating section to generate light;

an optical switching section to switch the light according to the image data and to output two-dimensional image signal;

a hologram displaying section to create and display hologram from the two-dimensional image signal by using difference of angle of vision between two eyes; and a light source lens to enlarge and project the hologram into space.

3. The apparatus according to claim 2, wherein the optical switching section comprises:

a digital micromirror device to receive red light; a digital micromirror device to receive blue light; and a digital micromirror device to receive green light through the optical switching.

4. The apparatus according to claim 2, wherein the two-dimensional image signal transmits the image pixels and the mask pitch projects the two-dimensional image signal to the light source lens through the transparent slits.

5. The apparatus according to claim 1, wherein the hologram processing section comprises: a light-emitting lamp;

a red mirror, a green mirror and a blue mirror to separate the light into primary color light of red, green and blue, respectively, according to the image data;

a mono liquid crystal panel to reflect light of colors other than the primary colors and to project only the primary color light;

a LCD panel to re-synthesize the projected light of the primary colors to create a two-dimensional image;

a combiner tube to create the hologram from the two-dimensional image by color combination; and a lens to enlarge and project the created hologram.

6. The apparatus according to claim 1, further comprising:

a displaying section to receive the diagnosis data and to display it to the user according to control of the control section.

7. The apparatus according to claim 6, wherein the control section converts a mode of the terminal into a hologram mode according to a choice of the user, and transmits image data regarding the user photographed through the camera section to an emergency center through the RF processing section.

8. A method for displaying hologram of a mobile communication terminal, comprising:

performing medical diagnosis on a user through a medical diagnosis section contacting with the user and outputting corresponding diagnosis data;

comparing the diagnosis data with a previously stored medical reference value, and setting up a call at the mobile communication terminal with a preset emergency center to transmit the diagnosis data only if the comparison reveals an abnormal state of the user;

photographing the user through a camera section of the mobile communication terminal and transmitting corresponding image data to the preset emergency center; and demodulating analog image data received from the emergency center to digital image data, creating a hologram from a two-dimensional image signal by using the demodulated digital image data, and displaying the hologram from a hologram display section of the mobile communication terminal to the user, wherein the process of displaying the hologram comprises steps of:

backing up and image-processing the digital image data:

switching light projected from light source according to the processed image data and projecting the light to transparent slits of a mask pitch through image pixels to display the hologram; and enlarging the hologram through a light source lens and projecting the enlarged hologram to space, wherein the image pixels are separated from each other with a predetermined gap, and the mask pitch has masks and transparent slits, wherein each transparent slit is located at a middle boundary of every two image pixels and the mask pitch is located at the front of the image panel with a predetermined distance.

9. The method according to claim 8, wherein digital micromirror devices are used to receive red light, blue light and green light when switching the light projected from the light source.

10. The method according to claim 8, wherein the process of displaying the hologram comprises steps of:

backing up and image-processing the digital image data;

separating light emitted from a lamp into primary color light of red, green, and blue by a red mirror, a green mirror and a blue mirror according to the processed image data;

reflecting light of colors other than the primary colors of the separated light and projecting only the primary color light by a mono liquid crystal panel;

resynthesizing the projected respective primary color light to create two-dimensional image by a LCD panel;

creating the hologram from the two-dimensional image through color combination by a combiner tube; and enlarging and projecting the created hologram by a lens.

* * * * *

UNITED STATES PATENT AND TRADEMARK OFFICE
CERTIFICATE OF CORRECTION

| | | |
|---|---|---|
| PATENT NO. | : 7,693,316 B2 | Page 1 of 1 |
| APPLICATION NO. | : 10/943482 | |
| DATED | : April 6, 2010 | |
| INVENTOR(S) | : Tae Hyo Lee | |

It is certified that error appears in the above-identified patent and that said Letters Patent is hereby corrected as shown below:

On the cover of the patent, between item (65) and (51), insert:

-- (30)     Foreign Application Priority Data
November 25, 2003     (KR)     10-2003-0084051 --.

Signed and Sealed this

Fifteenth Day of June, 2010

David J. Kappos
*Director of the United States Patent and Trademark Office*